(12) United States Patent
Sachs et al.

(10) Patent No.: US 8,729,479 B1
(45) Date of Patent: May 20, 2014

(54) MOLECULAR BREAST IMAGING APPARATUS AND METHOD FOR CONCURRENT DUAL-BREAST IMAGING

(71) Applicant: General Electric Company, Schenectady, NY (US)

(72) Inventors: Jonathan Sachs, Haifa (IL); Yaron Hefetz, Kibbutz Alonim (IL)

(73) Assignee: GE Medical Systems Israel Ltd., Tirat Carmel (IL)

( * ) Notice: Subject to any disclaimer, the term of this patent is extended or adjusted under 35 U.S.C. 154(b) by 0 days.

(21) Appl. No.: 13/727,753

(22) Filed: Dec. 27, 2012

(51) Int. Cl.
*G01T 1/161* (2006.01)
*A61B 6/00* (2006.01)

(52) U.S. Cl.
CPC ..................................... *A61B 6/502* (2013.01)
USPC .................................................... 250/363.02

(58) Field of Classification Search
CPC ...... A61B 6/502; A61B 5/4312; A61B 6/484; A61B 5/0691; G01T 2207/30068; G01N 33/57415
USPC .................. 250/363.01–363.1, 362; 378/98.8
See application file for complete search history.

(56) References Cited

U.S. PATENT DOCUMENTS

| | | | | |
|---|---|---|---|---|
| 5,451,789 A * | 9/1995 | Wong et al. | ............. | 250/363.03 |
| 5,528,043 A * | 6/1996 | Spivey et al. | ............ | 250/370.09 |
| 7,728,303 B2 * | 6/2010 | Mori et al. | ............... | 250/370.11 |
| 8,115,171 B2 | 2/2012 | Blevis | | |
| 8,139,712 B2 * | 3/2012 | Kojima | ........................... | 378/37 |
| 8,217,357 B2 | 7/2012 | Stein et al. | | |
| 8,594,274 B2 * | 11/2013 | Hoernig et al. | .................. | 378/22 |
| 2010/0034734 A1 | 2/2010 | O'Connor et al. | | |
| 2010/0104505 A1 | 4/2010 | O'Connor | | |
| 2010/0261997 A1 | 10/2010 | Ren et al. | | |
| 2010/0329418 A1 | 12/2010 | Blevis | | |
| 2011/0158384 A1 * | 6/2011 | Beekman | ........................ | 378/37 |
| 2011/0216880 A1 | 9/2011 | Blevis | | |
| 2011/0248174 A1 | 10/2011 | O'Connor et al. | | |
| 2012/0148016 A1 | 6/2012 | Blevis | | |
| 2012/0263273 A9 | 10/2012 | Stein et al. | | |
| 2013/0108016 A1 * | 5/2013 | Tonami | ........................... | 378/37 |
| 2013/0131509 A1 * | 5/2013 | Rafaeli et al. | ................. | 600/436 |

* cited by examiner

*Primary Examiner* — Kiho Kim

(74) *Attorney, Agent, or Firm* — General Electric Company; Lucas Divine

(57) ABSTRACT

A nuclear medicine mammography system and method for conducting concurrent examinations of both breasts of a patient, thereby reducing examination time in molecular breast imaging. The system comprises first and second pairs of generally opposed articulatable gamma photon detectors, wherein each pair of detectors can be arranged to image a respective breast independently from the other pair of detectors. In one or more embodiments, the first detector pair is dedicatedly oriented in a first orientation and the second detector pair is dedicatedly oriented in a second, different orientation.

19 Claims, 11 Drawing Sheets

MOLECULAR BREAST IMAGING APPARATUS AND METHOD FOR CONCURRENT DUAL-BREAST IMAGING

BACKGROUND OF THE INVENTION

The present invention relates generally to nuclear medicine imaging, and more particularly to molecular breast imaging using nuclear medicine.

U.S. Pat. No. 8,115,171, assigned to General Electric Company and titled "Gamma Camera for Performing Nuclear Mammography Imaging" (herein incorporated by reference), describes a system for performing "molecular breast imaging", or "MBI". MBI typically involves the injection of a radiotracer into a patient wherein the radiotracer is carried by the bloodstream throughout the patient's body while emitting high-energy gamma photons which can be detected by a detection and imaging system, such as the system of CZT-based detectors described in the aforementioned patent. Nuclear imaging systems (also called molecular imaging systems) such as described in the aforementioned patent work by detecting the distribution of gamma ray emanations throughout the patient's body or from within a specific region of interest (ROI). Areas where the gamma ray emanations are remarkably higher than would be the case for normal tissue at that area indicate an increased amount of uptake of the radiotracer in that tissue, possibly indicating cancerous tissue, while areas where the gamma ray emanations are remarkably lower than would be the case for normal tissue at that area indicate a decreased amount of uptake of radiotracer in that tissue area, possibly indicating necrotic or dead tissue. Thus, MBI utilizes nuclear/molecular imaging focused on the breast and surrounding ROIs (e.g., the axillary lymph nodes), primarily to detect or screen for breast cancer.

FIG. 1 illustrates the typical workflow involved in conventional MBI, which is very similar to the workflow involved in X-ray based mammography. In FIG. 1A, a patient's breast (in this case, the patient's right breast 16) is positioned between an upper gamma detector 12 and a lower gamma detector 14 (or, the upper and lower detectors 12/14 are positioned so as to be adjacently above and below the breast, respectively) and the detectors 12/14 are moved toward each other so as to immobilize and/or lightly compress the selected breast. In FIG. 1A, the detectors are oriented essentially directly above and below the breast, in what is known in the art as the cranio-caudal (CC) orientation. Once the detectors are in place in this orientation for sufficient time to gather enough gamma photons for subsequent image reconstruction, the next step in the workflow is to move the detectors apart from each other and place them in the mediolateral-oblique (MLO) orientation, as shown in FIG. 1B. Here again, the detectors 12/14 may immobilize and/or lightly compress the breast and remain in position long enough to receive sufficient gamma photon counts. Then, detectors 12/14 are moved apart and the patient and/or detectors are positioned such that the other breast 18 can be imaged, such as in the CC orientation as illustrated in FIG. 1C. The final step is then to reorient the detectors to the MLO orientation, as shown in FIG. 1D. Those skilled in the art will recognize that other sequences or workflows other than that illustrated in FIGS. 1A-1D may also be performed. For example, both CC orientations may be done first, and then the two MLO orientations, or any combination of FIGS. 1A-1D.

In the conventional prior art MBI workflows exemplified by FIG. 1, and as described in the aforementioned patent, only one pair of detectors is used. This is similar to the systems utilized by conventional X-ray based mammography, wherein one pair of paddles/detectors is used to compress and image one breast at a time. However, one drawback for MBI workflows in particular is that it can take quite a long time at each of the four positions shown in FIGS. 1A-1D to gather sufficient gamma photon counts to produce a suitable image. (Typically it takes much longer for a pair of gamma detectors to produce a suitable image than it takes for a pair of X-ray paddles/detectors to do so.) In addition to just the amount of time it takes, there is also the amount of discomfort that the patient must endure while the full workflow is completed. It would be desirable, therefore, to provide an improved MBI system and workflow which is quicker so as to reduce the amount of time spent and discomfort experienced by patients undergoing an MBI imaging procedure.

SUMMARY OF THE INVENTION

In one set of embodiments of the present invention, there is provided a nuclear medicine mammography system for conducting examinations of both breasts of a patient, comprising first and second pairs of generally opposed articulatable gamma photon detectors, wherein each pair of detectors can be arranged to image a respective breast independently from the other pair of detectors, and wherein both breasts can be imaged concurrently. Each pair of detectors can be arranged in at least two imaging orientations, such as cranio-caudal and mediolateral-oblique. The system may be configured to provide a first configuration in which each of the detector pairs is oriented in a respective first orientation, and a second configuration in which each of the detector pairs is oriented in a respective second orientation that is different from the respective first orientation. In each of the first and second configurations, both of the detector pairs may oriented in the same orientation or in different orientations. For example, in the first configuration both detector pairs may be oriented in a cranio-caudal orientation, and in the second configuration both detector pairs may be oriented in a mediolateral-oblique orientation. Alternatively, in the first configuration one detector pair may be oriented in a cranio-caudal orientation and the other detector pair may be oriented in a mediolateral-oblique orientation, and in the second configuration the one detector pair may be oriented in a mediolateral-oblique orientation and the other detector pair may be oriented in a cranio-caudal orientation.

In another set of embodiments of the present invention, there is provided a method for conducting examinations of both breasts of a patient, comprising the steps of: (a) providing a nuclear medicine mammography system having first and second pairs of generally opposed articulatable gamma photon detectors, wherein each pair of detectors can be arranged to image a respective breast independently from the other pair of detectors; (b) configuring the system in a first configuration in which each detector pair is oriented in a respective first orientation with respect to the patient; (c) conducting a first imaging of both breasts of the patient by concurrently operating both detector pairs; (d) configuring the system in a second configuration in which each detector pair is oriented in a respective second orientation with respect to the patient that is different from the respective first orientation; and (e) conducting a second imaging of both breasts of the patient by concurrently operating both detector pairs. Each pair of detectors can be arranged in at least two imaging orientations, such as cranio-caudal and mediolateral-oblique. Methods according to this set of embodiments may further comprise the step of: (f) prior to each of steps (c) and (e), positioning the patient with each breast positioned between a respective pair of detectors. In each of the first and second configurations, both of the detector pairs may be oriented in the same orientation or in different orientations.

In yet another set of embodiments of the present invention, there is provided a nuclear medicine mammography system for conducting examinations of both breasts of a patient, comprising first and second pairs of generally opposed articulatable gamma photon detectors, wherein each pair of detectors can be arranged to image a respective breast independently from the other pair of detectors. The first detector pair is dedicatedly oriented in a first orientation and the second detector pair is dedicatedly oriented in a second orientation that is different from the first orientation. The system is configured to provide a first configuration in which the first detector pair can be arranged to image the right breast and the second detector pair can be arranged to image the left breast, and a second configuration in which the first detector pair can be arranged to image the left breast and the second detector pair can be arranged to image the right breast, wherein in each of the first and second configurations both breasts can be imaged concurrently. One detector pair can be dedicated to a generally cranio-caudal, mediolateral-oblique or mediolateral orientation, while the other detector pair is dedicated to a different orientation. Each detector pair is oriented in a respective orientation in both the first and second configurations. The system may further comprise first and second platens operably connected to the first and second detector pairs, respectively, and a turntable operably connecting the first and said platens to a gantry.

In an additional set of embodiments of the present invention, there is provided a method for conducting examinations of both breasts of a patient, comprising the steps of: (a) providing a nuclear medicine mammography system having first and second pairs of generally opposed articulatable gamma photon detectors operably connected to respective first and second platens, and a turntable operably connecting said first and second platens to a gantry; (b) configuring the system in a first configuration in which the first detector pair is arranged to image the right breast and the second detector pair is arranged to image the left breast; (c) conducting a first imaging of both breasts of the patient by concurrently operating both detector pairs; (d) configuring the system in a second configuration in which the first detector pair is arranged to image the left breast and the second detector pair is arranged to image the right breast; and (e) conducting a second imaging of both breasts of the patient by concurrently operating both detector pairs. The method may further comprise the step, prior to each of steps (c) and (e), of (f) positioning the system and/or the patient such that each breast is positioned between a respective pair of detectors. One or both of the configuring steps may be performed by rotating or moving the turntable so as to place each platen and its associated detector pair in position for immobilizing and imaging a respective breast. The first detector pair is dedicatedly oriented in a first orientation and the second detector pair is dedicatedly oriented in a second orientation that is different from said first orientation. For example, one detector pair may be oriented in a cranio-caudal orientation and the other may be oriented in a mediolateral or mediolateral-oblique orientation. The configuring steps may include articulating one or both of the detectors in each detector pair so as to immobilize each respective breast for imaging.

In a further set of embodiments of the present invention, there is provided a system and method according to one or more of the above embodiments in which a third pair of generally opposed gamma photon detectors is provided in addition to the aforementioned two detector pairs. The third pair of detectors may have a length greater than that of either of the first and second pairs, so as to be configured to image both breasts concurrently, such as in a generally cranial-caudal orientation.

In yet a further set of embodiments of the present invention, there is provided a system and method according to one or more of the above embodiments in which one or two gamma photon detectors is provided in addition to the aforementioned two or three detector pairs, for imaging the lymph nodes. Such imaging of the lymph nodes may be performed at the same time that both breasts are being imaged concurrently.

DETAILED DESCRIPTION OF THE INVENTION

Figure 1:
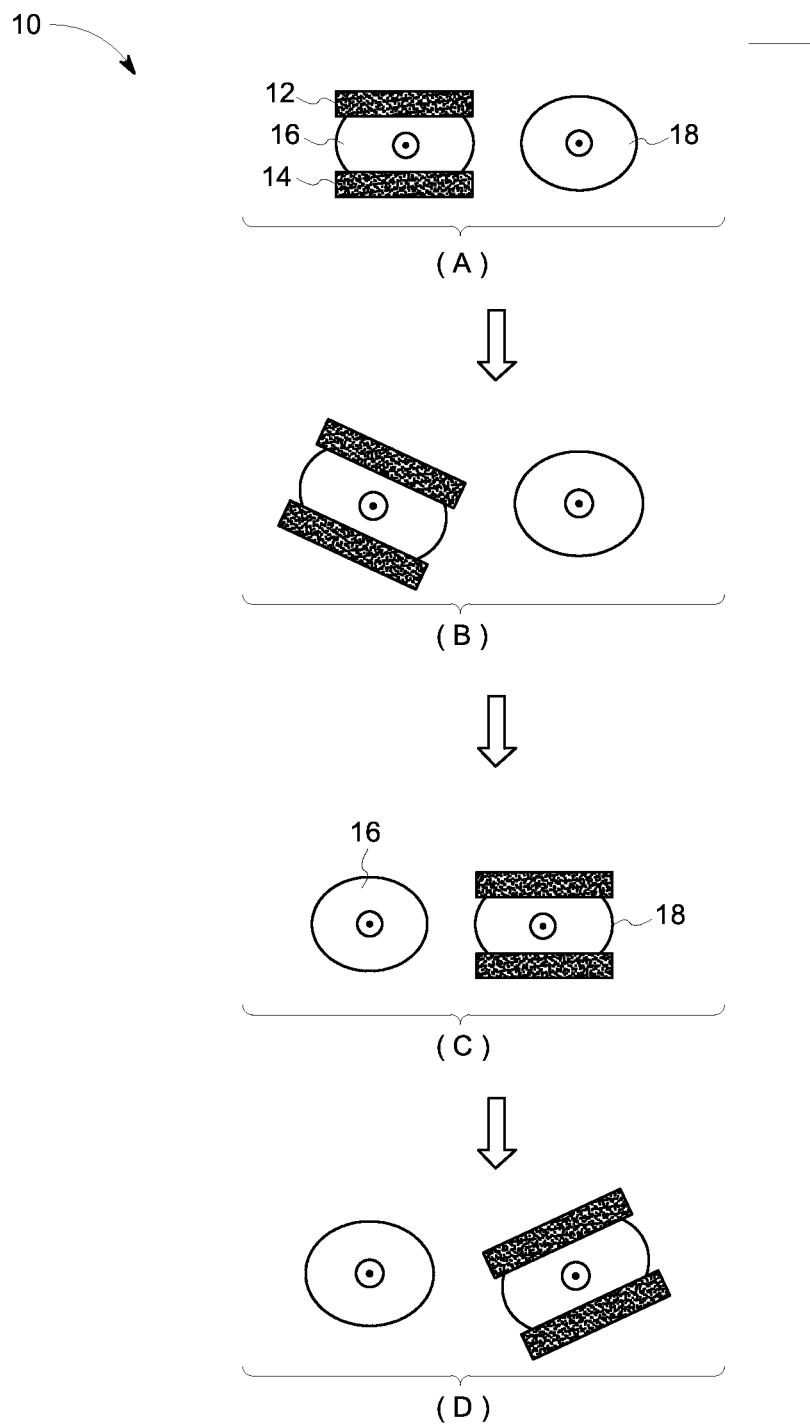
FIG. 1 is a schematic representation of a typical breast imaging procedure according to the prior art.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware or circuitry. For example, one or more of the functional blocks (e.g., processors or memories) may be implemented in a single piece of hardware (e.g., a general purpose signal processor or random access memory, hard disk, or the like); likewise, a single functional block may be implemented in more than one piece of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, any references to a particular embodiment or example of the present invention are not intended to be interpreted as excluding the existence of additional embodiments or examples that also incorporate the recited features. Moreover, unless explicitly stated to the contrary, embodiments "comprising" or "having" an element or a plurality of elements having a particular property may include additional such elements not having that property.

Various embodiments of the present invention provide a system and method for performing molecular breast imaging using nuclear medicine techniques. A technical effect of the various embodiments is to provide a molecular breast imaging system that is configured to selectively provide at least two detector pair configurations for imaging both breasts at the same time, thereby reducing the amount of time needed for examinations as compared to conventional approaches in which only one breast at a time is examined.

Figure 2:
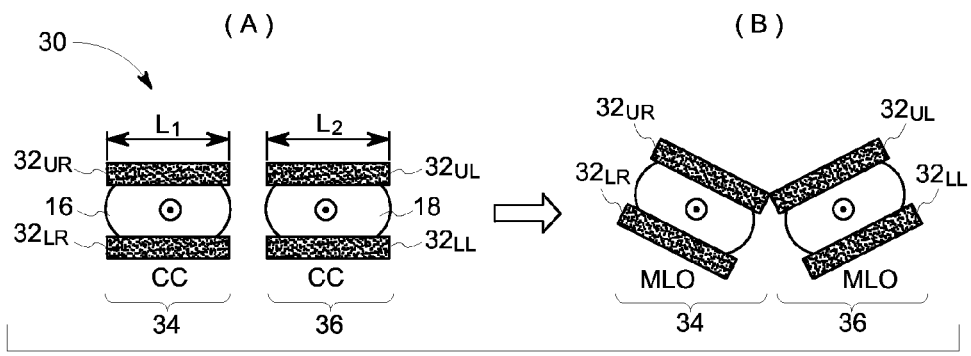
FIG. 2 is a schematic representation of a breast imaging procedure according to a first embodiment of the present invention.
Figure 3:
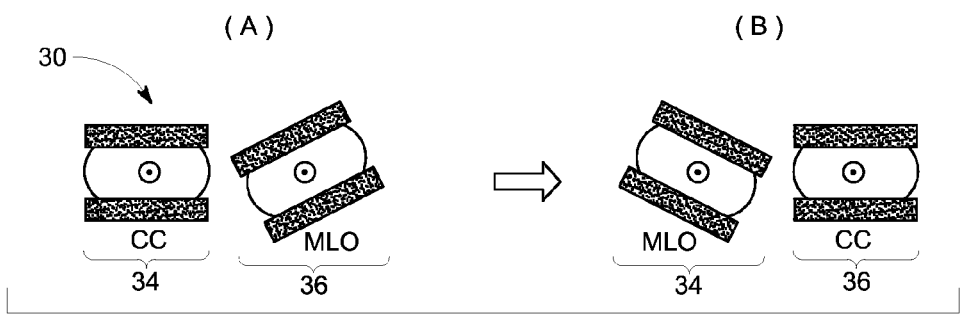
FIG. 3 is a schematic representation of a breast imaging procedure according to a second embodiment of the present invention.

To assist the reader in understanding the embodiments of the present invention that are disclosed, all reference numbers used herein are summarized below, along with the elements they represent:

10 Prior art system
12 Upper detector
14 Lower detector
16 Right breast
18 Left breast
20 Upper part of the breast
22 Lower part of the breast
30 System according to the present invention
32 Detector
$32_{UR}$ Upper right detector
$32_{LR}$ Lower right detector
$32_{UL}$ Upper left detector
$32_{LL}$ Lower left detector
$32_U$ Upper detector
$32_L$ Lower detector
32' (Nominally) left detector
32" (Nominally) right detector
34 First detector pair
36 Second detector pair
38 Third detector pair
40 Additional detector for imaging lymph nodes
50 Platen
$50_{CC}$ Platen for detector pair dedicated to cranio-caudal orientation
$50_{ML}$ Platen for detector pair dedicated to mediolateral orientation
61 Detector 1
62 Detector 2
63 Detector 3
64 Detector 4
71 Detector mover/controller 1
72 Detector mover/controller 2
73 Detector mover/controller 3
74 Detector mover/controller 4
81 Platen 1
82 Platen 2
91 Platen mover/controller 1
92 Platen mover/controller 2
93 Turntable
94 Turntable mover/controller
95 Gantry
100 Method for using one or more embodiments of the present invention
110 Step (a) of providing a system
120 Step (b) of configuring the system in a first configuration
130 Step (c) of conducting a first imaging
140 Step (d) of configuring the system in a second configuration
150 Step (e) of conducting a second imaging
160 Step (f1) of positioning the patient and/or system
170 Step (f2) of positioning the patient and/or system
200 Method for using one or more embodiments of the present invention
210 Step (a) of providing a system
220 Step (b) of configuring the system in a first configuration
230 Step (c) of conducting a first imaging
240 Step (d) of configuring the system in a second configuration
250 Step (e) of conducting a second imaging
260 Step (f1) of positioning the patient and/or system
270 Step (f2) of positioning the patient and/or system
(A) First configuration of the two detector pairs
(B) Second configuration of the two detector pairs
$L_1$ Length of first detector pair
$L_2$ Length of second detector pair
$L_3$ Length of second detector pair (shortened)
$L_4$ Length of third detector pair (elongated)
CC Cranio-caudal detector pair orientation
MLO Mediolateral-oblique detector pair orientation
ML Mediolateral detector pair orientation
LN Lymph node detector (pair) orientation
CW Clockwise direction
CCW Counter-clockwise direction Referring now to the drawings, FIGS. 2 and 3 show schematic representations of first and second embodiments, respectively, of the present invention. In these embodiments, a nuclear medicine mammography system 30 for conducting examinations of both breasts 16/18 of a patient comprises first and second pairs 34/36 of generally opposed articulatable gamma photon detectors 32, wherein each pair of detectors can be arranged to image a respective breast independently from the other pair of detectors, and wherein both breasts can be imaged concurrently. Each pair of detectors 34/36 can be arranged in at least two imaging orientations, such as the cranio-caudal (CC) and mediolateral-oblique (MLO) orientations. The system 30 may be configured to provide a first configuration or arrangement (A) in which each of the detector pairs is oriented in a respective first orientation, and a second configuration or arrangement (B) in which each of the detector pairs is oriented in a respective second orientation that is different from the respective first orientation. In each of the first and second configurations, both of the detector pairs may be oriented in the same orientation; for example, as shown in FIG. 2, in the first configuration (A) both detector pairs 34/36 may be oriented in a cranio-caudal orientation, and in the second configuration (B) both detector pairs may be oriented in a mediolateral-oblique orientation. Alternatively, in each of the first and second configurations the detector pairs may be oriented in different orientations; for example, as shown in FIG. 3, in the first configuration (A) one detector pair 34 may be oriented in a cranio-caudal orientation and the other detector pair 36 may be oriented in a mediolateral-oblique orientation, and in the second configuration (B) the one detector pair 34 may be oriented in a mediolateral-oblique orientation and the other detector pair 36 may be oriented in a cranio-caudal orientation.

As used herein, the term "orientation" refers to the MLO, CC and ML (mediolateral) detector pair orientations, and the term "configuration" refers to the two system configurations, arrangements or sequences for each embodiment. Note the (A) and (B) notations in FIGS. 2-7, indicating the two system/detector pair configurations for each embodiment. It should be noted that although the arrow drawn between configurations (A) and (B) can mean that configuration (A) is performed first, followed by configuration (B), it is equally possible that configuration (B) is performed first, followed by configuration (A). Also note that each configuration or step of the disclosed embodiments can include not only arranging the detectors 32 as illustrated, but can also optionally include one or more steps of waiting to obtain sufficient counts, preprocessing the counts (e.g., converting, conditioning, thresholding, discriminating, summing, histogramming, storing, etc.), creating/storing/displaying images, setting/resetting flags or registers, displaying icons or data, alerting/updating the operator or clinician, etc. Further, as used herein, the descriptors "right" and "left" to describe the patient's breasts and/or the corresponding detector pairs refer to the patient's right and left breasts, respectively, as viewed by the patient. Thus, for each pair of breasts illustrated in FIGS. 2-7, all of which are shown in frontal view, the breast to the left in each illustration is the patient's right breast, and the breast to the right in each illustration is the patient's left breast.

Figure 4:
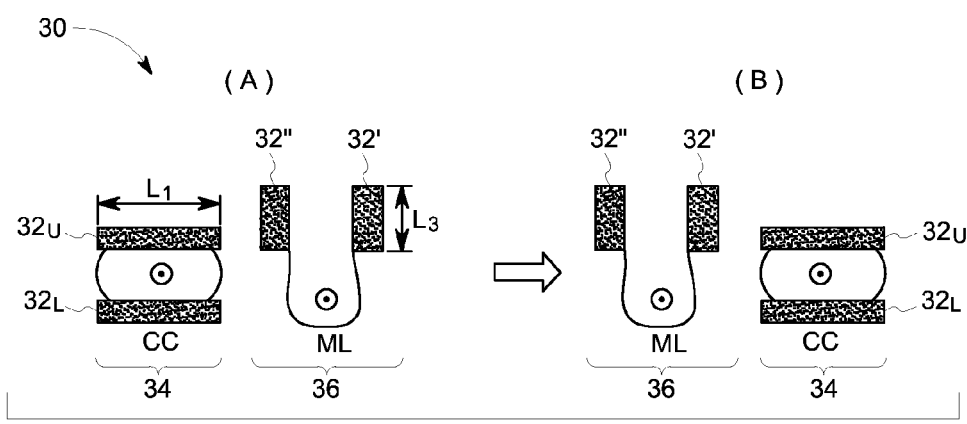
FIG. 4 is a schematic representation of a breast imaging procedure according to a third embodiment of the present invention.
Figure 8:
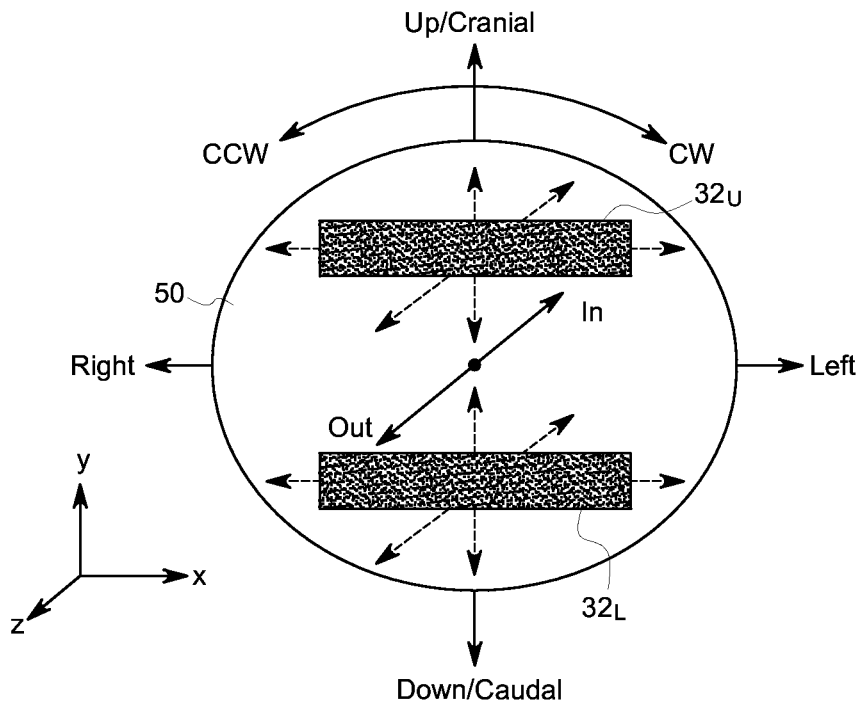
FIG. 8 is a schematic representation of a platen supporting two detectors and illustrating various degrees of freedom according to an embodiment of the present invention.
Figure 10:
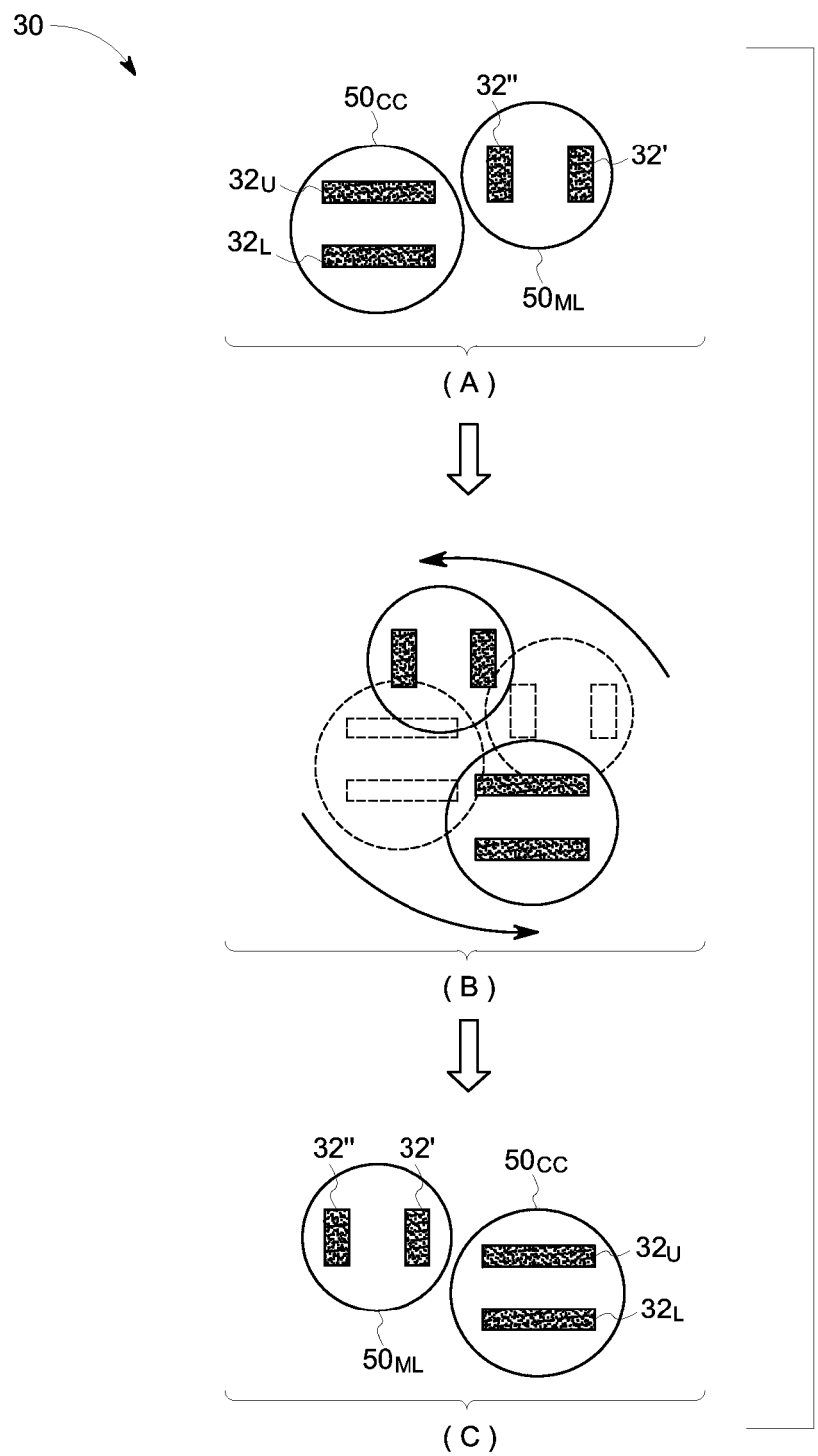
FIG. 10 is a schematic representation of two platens each supporting two detectors according to an embodiment of the present invention.

FIG. 4 shows a schematic representation of a third embodiment of the present invention. In this embodiment, a nuclear medicine mammography system 30 is presented, comprising first and second pairs 34/36 of generally opposed articulatable gamma photon detectors, wherein each pair of detectors can be arranged to image a respective breast independently from the other pair of detectors. The first detector pair 34 is dedicatedly oriented in a first orientation and the second detector pair 36 is dedicatedly oriented in a second orientation that is different from said first orientation. (Although each detector pair is dedicated to a particular orientation, one or both detector pairs may also be articulatable/moveable with respect to one or more axes, directions or degrees of freedom.) The system 30 is configured to provide a first configuration (A) in which the first detector pair 34 can be arranged to image the right breast 16 and the second detector pair 36 can be arranged to image the left breast 18, and a second configuration (B) in which the first detector pair 34 can be arranged to image the left breast 18 and the second detector pair 36 can be arranged to image the right breast 16. In each of said first and second configurations, both breasts can be imaged concurrently. In FIG. 4, configuration (A), the first detector pair 34 is shown as being oriented in a CC orientation and the second detector pair 36 is shown as being oriented in an ML orientation, but other dedicated orientations can also be used, such as MLO. Once the patient has been imaged in configuration (A), the two detector pairs can be switched, as shown in configuration (B). This can be accomplished by placing the detector pairs on "switchable" platens as illustrated in FIG. 10. Here the first detector pair $32_U/32_L$ is mounted on a first platen $50_{CC}$ in a CC orientation, and the second detector pair 32'/32" is mounted on a second platen $50_{ML}$ in an ML orientation. In FIG. 10(a), the detector pairs/platens are placed in a first configuration (A) with the patient's breasts immobilized by and supported between respective detector pairs, and a first imaging step is commenced. Once sufficient counts have been detected, the platens are switched or revolved as illustrated in FIG. 10(b), shown here as counter-clockwise but which can also occur in a clockwise or other direction (or set of directions). As further described below, the platens $50_{CC}/50_{ML}$ may be moveably and controllably connected to a turntable for positioning or "switching" the left/right positions of the platens. The platens/detector pairs are then arranged in the second configuration (B) as illustrated in FIG. 10(c) in which each detector pair is associated with the opposite breast than was the case from configuration (A), with the patient's breasts immobilized by and supported between respective detector pairs, and a second imaging step is commenced. Although the platens 50 are illustrated in FIGS. 8 and 10 as oval-shaped, they may also be provided in other shapes. As further described below, mechanisms such as slots, standoffs, geared drives or the like may be provided to connect each detector 32 to a platen 50 and to provide for controlled movement/articulation of at least one of the detectors in each detector pair so as to place each detector pair into position to immobilize and image a respective breast.

Figure 5:
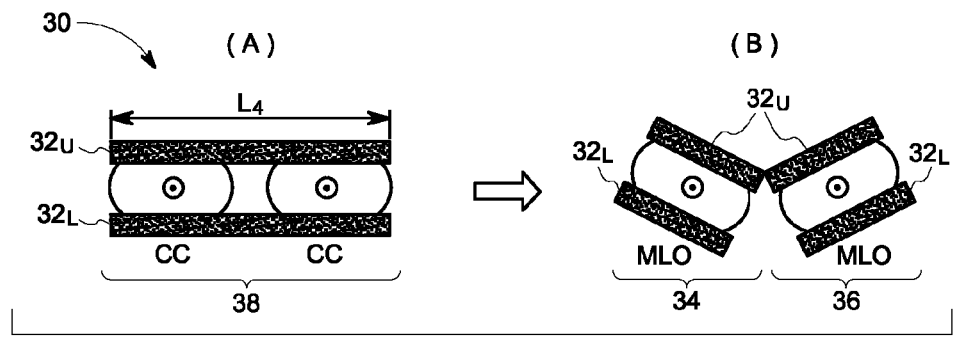
FIG. 5 is a schematic representation of a breast imaging procedure according to a fourth embodiment of the present invention.
Figure 6:
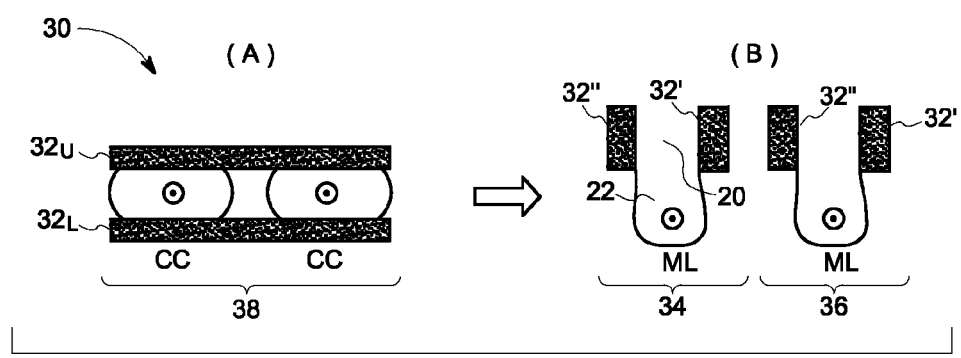
FIG. 6 is a schematic representation of a breast imaging procedure according to a fifth embodiment of the present invention.

FIGS. 5 and 6 show schematic representations of fourth and fifth embodiments, respectively, of the present invention. Whereas the first, second and third embodiments (FIGS. 2-4) feature two pairs of detectors, the fourth and fifth embodiments feature three pairs of generally opposed articulatable gamma photon detectors. In these embodiments, first and second pairs 34/36 of detectors are provided, as well as an additional third pair 38 of generally elongated detectors capable of immobilizing and imaging both breasts at the same time. As shown in FIGS. 5-6, the third pair 38 may comprise a top detector $32_T$ and a bottom detector $32_B$, each of which is capable of spanning both breasts. The lengths of the two elongated detectors $32_T/32_B$ can be different from each other, or (more preferably) they can have the same length $L_4$ as each other, which may be greater than the lengths $L_1$, $L_2$ and $L_3$ of the detectors illustrated in FIGS. 2-4, in which each detector is sized so as to immobilize and image only a single breast at a time. It should be noted that the lengths $L_1$ to $L_4$ illustrated in the figures are shown merely as a relative comparison with respect to each other, and are not intended as comparisons against any particular breast size. Generally, the lengths $L_1$ and $L_2$ of the two detector pairs 34/36 in FIGS. 2-3 may be generally the same, whereas the length $L_3$ of the ML-oriented detector pair 36 in FIG. 4 may be shorter than the length $L_1$ of the CC-oriented pair 34, and the length $L_4$ of the third detector pair 38 in FIGS. 5-6 may be longer than all of the foregoing detector lengths $L_1$ to $L_3$.

It should be noted that while FIGS. 5-6 show the third detector pair 38 as being in a generally CC-CC orientation, it is possible that the third detector pair can also be presented in other orientations, such as MLO-MLO. In such an orientation, the detector pair 38 may have a generally chevron-like or nested-V shape. Also, while the length $L_4$ of the third detector pair may be elongated so as to be capable of spanning and immobilizing both breasts of most patients, it is possible it may not adequately span both breasts of every patient.

As illustrated in FIGS. 5-6, the system 30 can be configured to provide a first configuration (A) in which the third detector pair 38 is presented for imaging both breasts concurrently using the single detector pair 38, followed by a second configuration (B) in which the first and second detector pairs 34/36 are presented for imaging both breasts concurrently using both detector pairs 34/36. Of course, configuration (B) can be provided for immobilization and imaging first, before configuration (A), if so desired. FIG. 5, configuration (B), shows both detectors pairs 34/36 as being in the MLO orientation, whereas FIG. 6, configuration (B), shows both detector pairs 34/36 as being in the ML orientation; in both of these embodiments (for FIGS. 5-6), the CC imaging is provided by the elongated detector pair 38 in configuration (A).

The system 30 can be designed so that one or more of the detector pairs 34/36/38 can be provided as a permanently attached portion of the gantry/system, or as an attachment which can be selectably mounted and removed from the gantry/system. For example, the third detector pair 38 can be provided as a single attachment, head or station, while the first and second detector pairs 34/36 can be provided together as another single attachment, head or station, or the first and second detector pairs can be provided as separate attachments, heads or stations.

Figure 7:
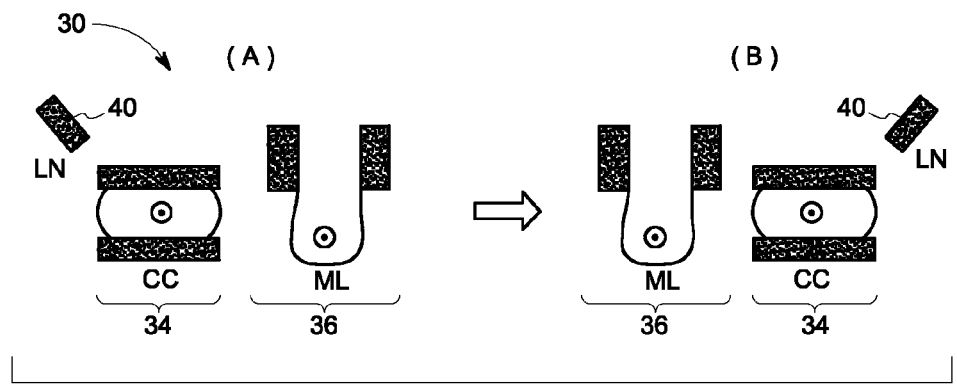
FIG. 7 is a schematic representation of a breast imaging procedure according to a sixth embodiment of the present invention.

FIG. 7 shows a schematic representation of a sixth embodiment of the present invention, in which one or two additional gamma photon detectors 40 can be added to any of the foregoing embodiments. This additional detector 40 is designed for use in a lymph node (LN) orientation; that is, placed adjacent the axillary (underarm) area for nuclear medicine imaging of the lymph nodes adjacent the breasts. Although FIG. 7 shows the additional detector 40 used with the third embodiment, it is possible to utilize the additional detector(s) 40 with any of the foregoing embodiments. One advantage of utilizing the additional detector(s) 40 is that they can be left in place to image one or more axillary views while the other detectors 34/36/38 are switched back and forth between configurations (A) and (B). Thus, the axillary imaging provided by the additional detector(s) 40 does not need to be synchronized with the beginning, duration or end of configurations (A) or (B), although it can be so synchronized if desired. (In other words, the timing of the placement and imaging of the additional detector(s) 40 can be performed essentially concurrent with but independent from the placement and imaging of the other detectors 34/36/38, without necessarily having to be synchronized therewith.)

The detectors 32 in each detector pair are arrangeable so as to be generally opposed from one another, in the sense that they may be positioned on opposing sides or areas of a patient's breast. For example, in FIG. 2, configuration (A), note that the upper right detector $32_{UR}$ is positioned above the right breast 16 and the lower right detector $32_{LR}$ is positioned below the right breast 16. Likewise, in FIG. 2, configuration (B), note that the upper right detector $32_{UR}$ is slantingly positioned above the right breast 16 and slightly toward the midsagittal or median plane, and the lower right detector $32_{LR}$ is slantingly positioned below the right breast 16 and slightly toward the patient's right side. In the figures, the detectors in each detector pair are shown as being generally parallel to each other. The detectors 32 may be radiation detectors utilizing cadmium-zinc-telluride (CZT), cadmium-telluride (CdTe) or any other suitable direct conversion material, or they may be scintillator-photomultiplier or scintillator-photodiode detectors or any other type capable of detecting gamma photons.

Figure 9:
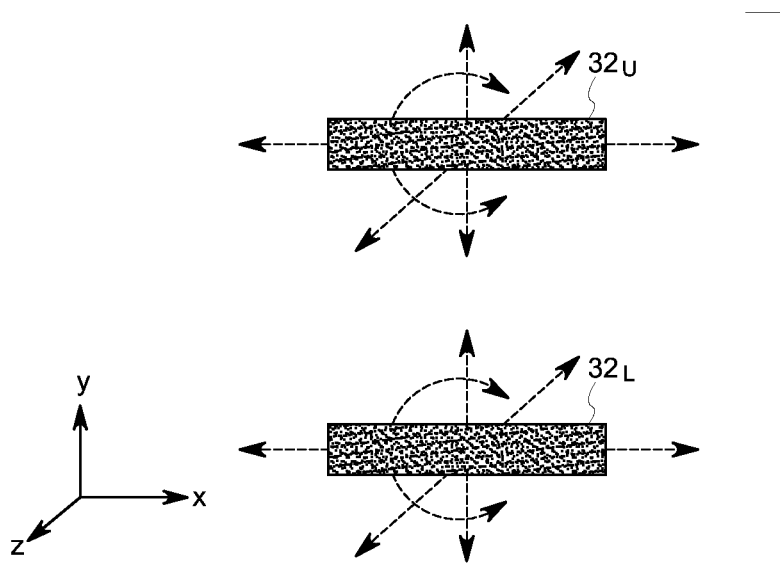
FIG. 9 is a schematic representation of two detectors illustrating their respective degrees of freedom according to an embodiment of the present invention.

One or both of the detectors 32 within each detector pair 34/36/38 should be capable of articulation, arrangement and/or movement with respect to one or more axes, directions or degrees of freedom. Preferably both detectors 32 in each detector pair are capable of such articulation. FIG. 8 shows a detector pair comprising an upper detector $32_U$ and a lower detector $32_L$, arranged here in a CC orientation. Both detectors may be articulatably mounted on a platen 50. The platen 50 is moveably mounted to a gantry portion 95 of the system 30 and is capable of moving up/down (in the y-direction), left/right (in the x-direction), in/out (in the z-direction) and/or clockwise/counter-clockwise (about the z axis) with respect to the gantry 95. Each detector $32_U/32_L$ is capable of moving up/down, left/right and/or in/out with respect to the platen 50. With the detectors mounted to a platen 50 as shown in FIG. 8, the platen can provide CW/CCW rotational movement to the detector pair (as well as up/down and/or left/right movement, if needed). Once the platen 50 is positioned, one or both of the detectors can be further articulated so that the patient's breast is suitably immobilized and captured for imaging. With the use of two platens connected to the gantry, with each carrying a respective pair of detectors, the platens can be moved one at a time or in unison, with each being adjusted as needed to capture the patient's breasts. Alternatively, as illustrated in FIG. 9, the detectors may be attached directly to the gantry without connection to an intervening platen. Here, each detector $32_U/32_L$ is not only capable of movement up/down, left/right and/or in/out, but is also capable of CW/CCW rotational movement as well. It should be noted that while FIGS. 8 and 9 show upper and lower detectors in a generally CC orientation, it is possible that the platen 50 and/or the detectors 32 can be rotated or moved to provide MLO, ML and other orientations as desired. The detector arrangements in FIG. 8 (with platen) and FIG. 9 (without platen) can be used with various ones of the preceding embodiments.

Figure 11:
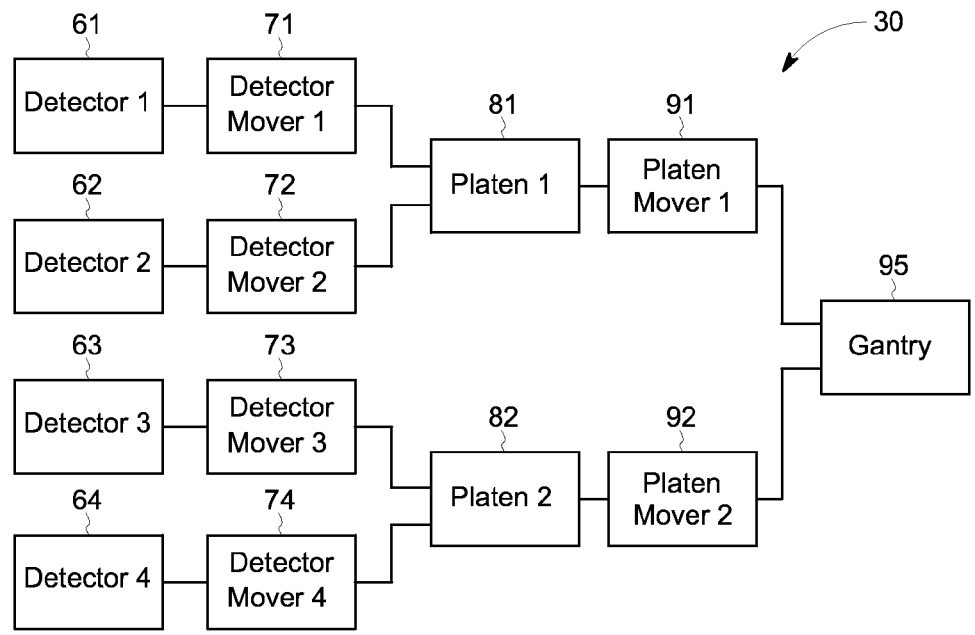
FIG. 11 is a block diagram of a nuclear medicine imaging system according to an embodiment of the present invention.
Figure 12:
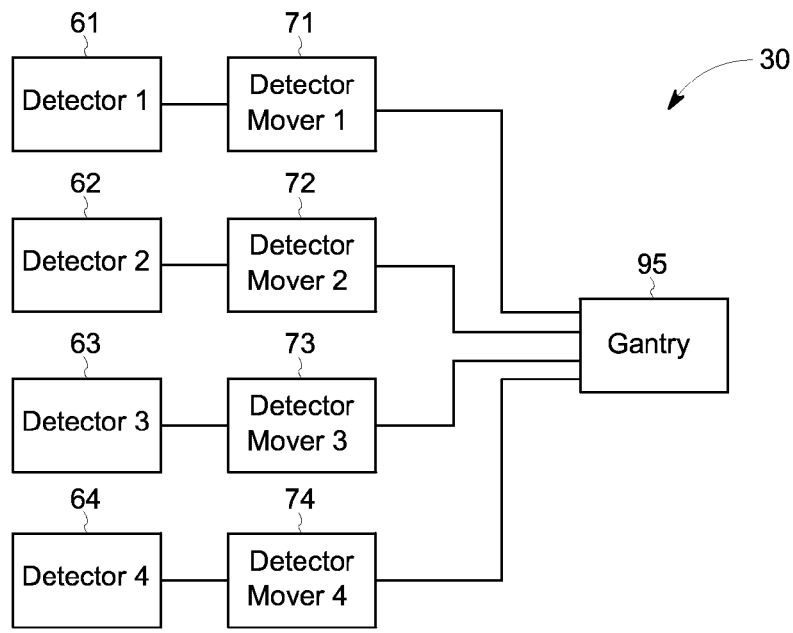
FIG. 12 is a block diagram of a nuclear medicine imaging system according to another embodiment of the present invention.
Figure 13:
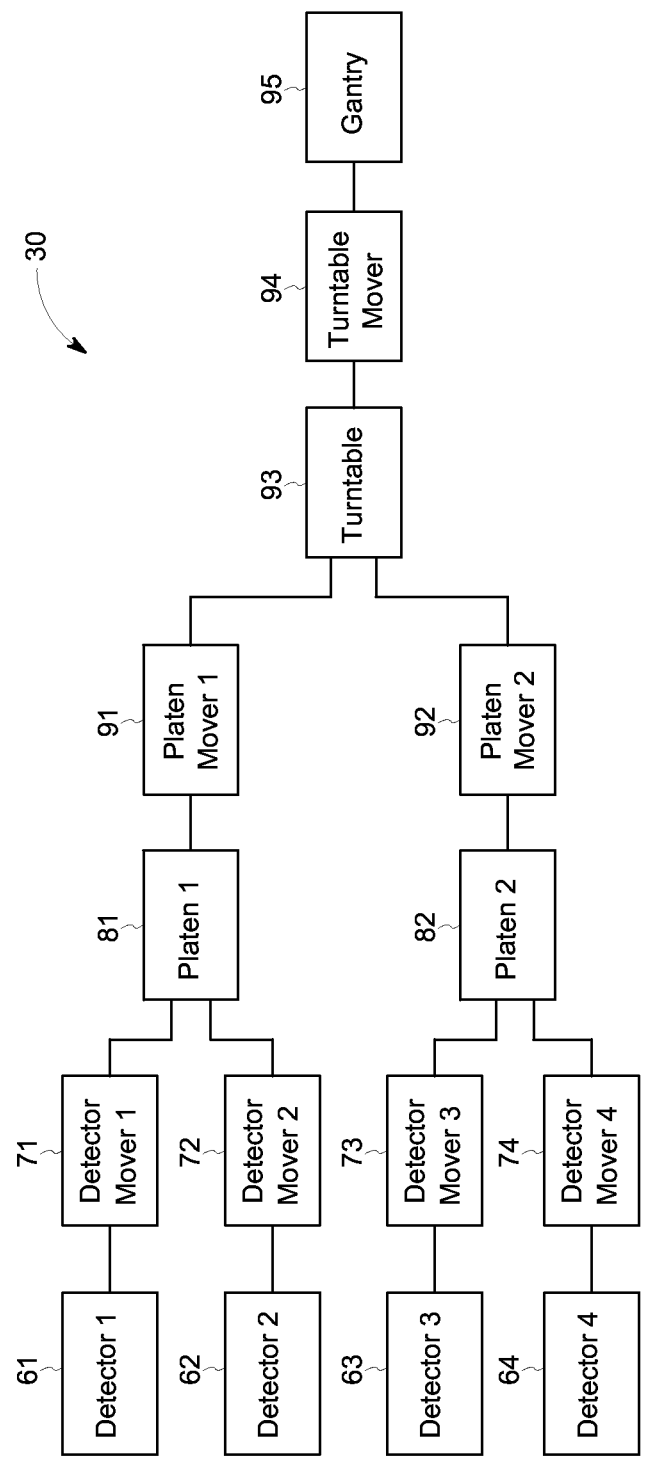
FIG. 13 is a block diagram of a nuclear medicine imaging system according to yet another embodiment of the present invention.

FIGS. 11-13 show block diagrams of a nuclear medicine mammography/MBI system 30 according to various embodiments of the present invention. FIG. 11 illustrates an arrangement which may be used with at least the first and second embodiments shown in FIGS. 2-3, in which a first pair of detectors 61/62 (34) is associated with a first platen 81 and a second pair of detectors 63/64 (36) is associated with a second platen 82, with the platens 81/82 being associated with a system gantry 95. Each detector may be associated with its respective platen via a respective detector mover/controller, which may comprise hardware/mechanisms and software/sub-systems for effecting and controlling movement/articulation of the detector along one or more axes or degrees of freedom. Alternatively, both detectors in each detector pair can be associated with a single mover/controller, rather than two separate movers/controllers. Likewise, each platen may be associated with the gantry via a respective platen mover/controller (which may comprise hardware/mechanisms and software/sub-systems for effecting and controlling movement/articulation of the platen along one or more axes or degrees of freedom), or both platens may be associated with a single platen mover/controller rather than two separate ones. In an exemplary embodiment of the invention, detector movers 71 and 73 may be missing such that detectors 61 and 63 may be attached to platens 81 and 82, respectively. In this case, detector movers 72 and 74 move detectors 62 and 64, respectively, towards detectors 61 and 63, respectively, to immobilize the respective breasts, and away from detectors 61 and 63, respectively, to release the respective breasts.

FIG. 12 illustrates an arrangement in which there are no platens, and instead the detectors 61-64 and their respective movers/controllers 71-74 may be directly connected to the gantry 95. As mentioned above, each detector pair (e.g., 61/62) may share a single detector mover/controller rather than each detector having its own.

FIG. 13 illustrates an arrangement which may be used with at least the third embodiment as shown in FIG. 4. Here, the two platens 81/82 and/or platen movers/controllers 91/92 are connected or associated with a turntable 93 or other structure for switching the left/right positions of the two detector pairs. This switching action is effected by the turntable mover/controller 94, which may comprise hardware/mechanisms and software/sub-systems for effecting and controlling the movement/articulation of the turntable. The turntable 93 is connected or associated with the turntable mover/controller 94, which in turn is connected or associated with the gantry 95. The turntable 93 may be a structure which rotates, thereby placing the platens into positions adjacent respective breasts in configurations (A) and (B), or it may comprise one or more mechanisms (e.g., slides, linkages, etc.) which provide motions other than or in addition to rotation, such as one or more translations.

It will be appreciated by those skilled in the art that some of the portions shown in FIGS. 11-13 as separate elements may be combined into single elements or sub-systems. For example, a detector and its respective mover/controller may be combined into a single detector/mover/controller sub-system; likewise for a platen and its mover/controller, and the turntable and its mover/controller. Other portions of the system 30 not shown in the figures, but well known to those skilled in the art and included within the scope of the present invention, include hardware and software for data processing, image reconstruction, displaying, user interaction, protocol selection/control, interfacing with clinical/hospital systems, interfacing with patient medical records and systems, etc.

Figure 14:
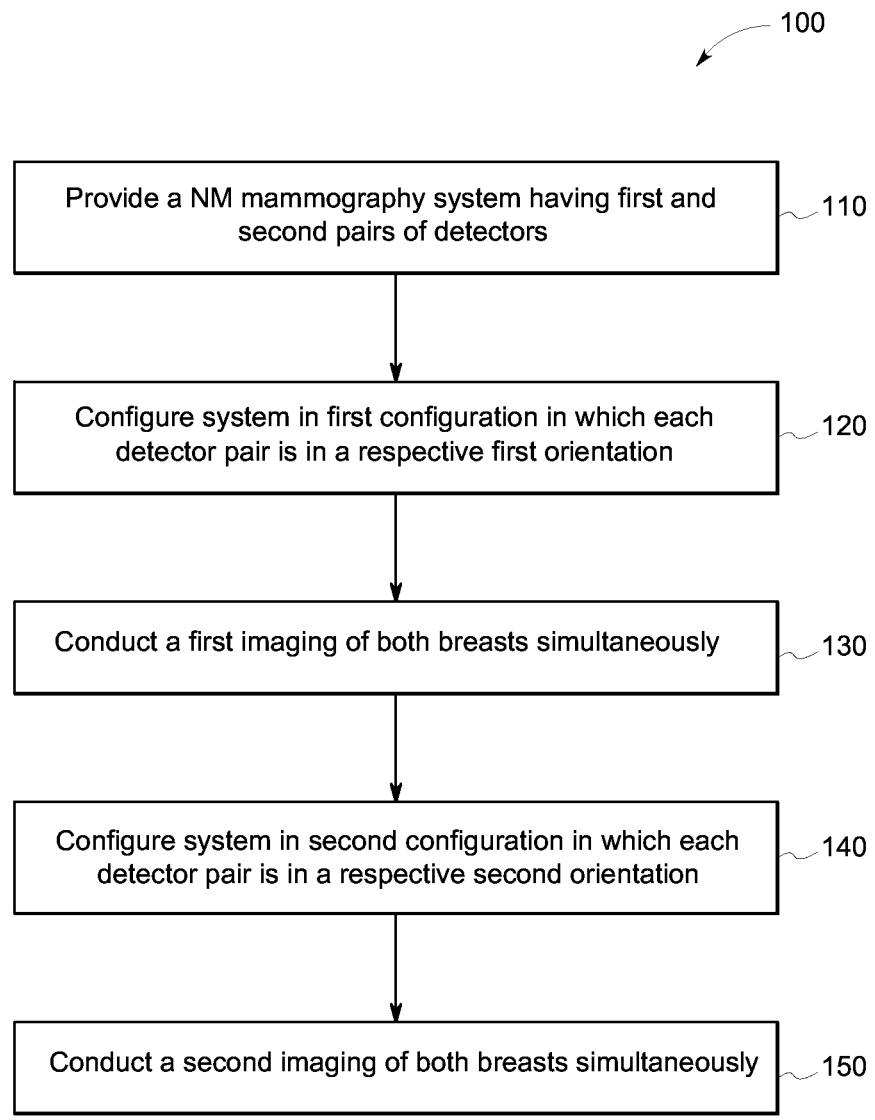
FIG. 14 is a flowchart showing the steps of a method according to one or more embodiments of the present invention.
Figure 15:
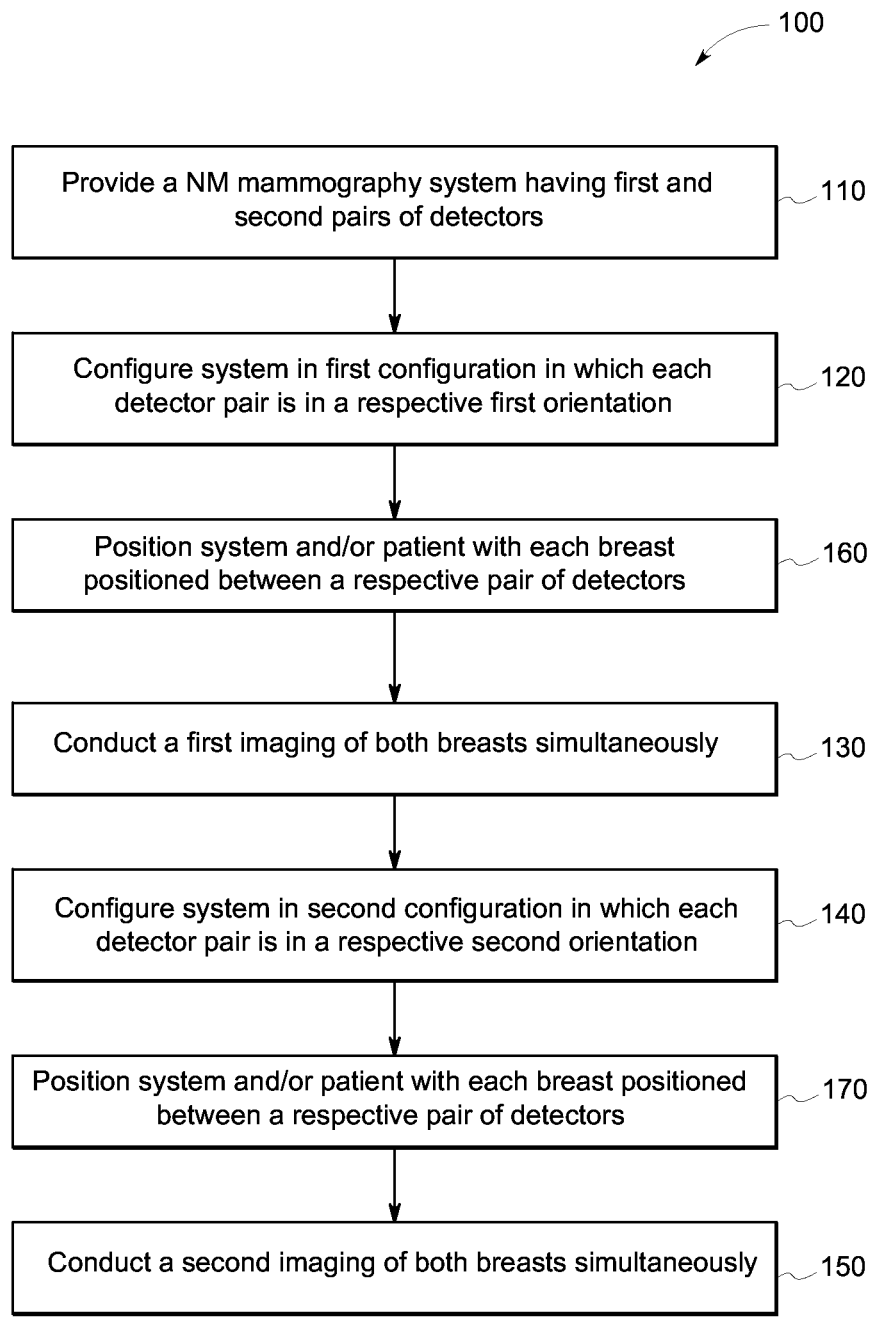
FIG. 15 is a flowchart showing the steps of another method according to one or more embodiments of the present invention.

FIGS. 14 and 15 illustrate methods 100 for conducting examinations of both breasts of a patient utilizing one or more of the systems 30 described above, such as the first and second embodiments. The method 100 may comprise the steps of: (110) providing a nuclear medicine mammography system having first and second pairs of generally opposed articulatable gamma photon detectors, wherein each pair of detectors can be arranged to image a respective breast independently from the other pair of detectors; (120) configuring the system in a first configuration in which each detector pair is oriented in a respective first orientation with respect to the patient; (130) conducting a first imaging of both breasts of the patient by concurrently operating both detector pairs; (140) configuring the system in a second configuration in which each detector pair is oriented in a respective second orientation with respect to the patient that is different from the respective first orientation; and (150) conducting a second imaging of both breasts of the patient by concurrently operating both detector pairs. Each pair of detectors can be arranged in at least two imaging orientations, including cranio-caudal and mediolateral-oblique orientations. As shown in FIG. 15, prior to each of steps (130) and (150), the method 100 may further comprise the step (160/170) of positioning the system (e.g., the detectors) and/or the patient such that each breast is positioned between a respective pair of detectors. In each of the first and second configurations, both of the detector pairs may be oriented in the same orientation, or the detector pairs may be oriented in different orientations.

Figure 16:
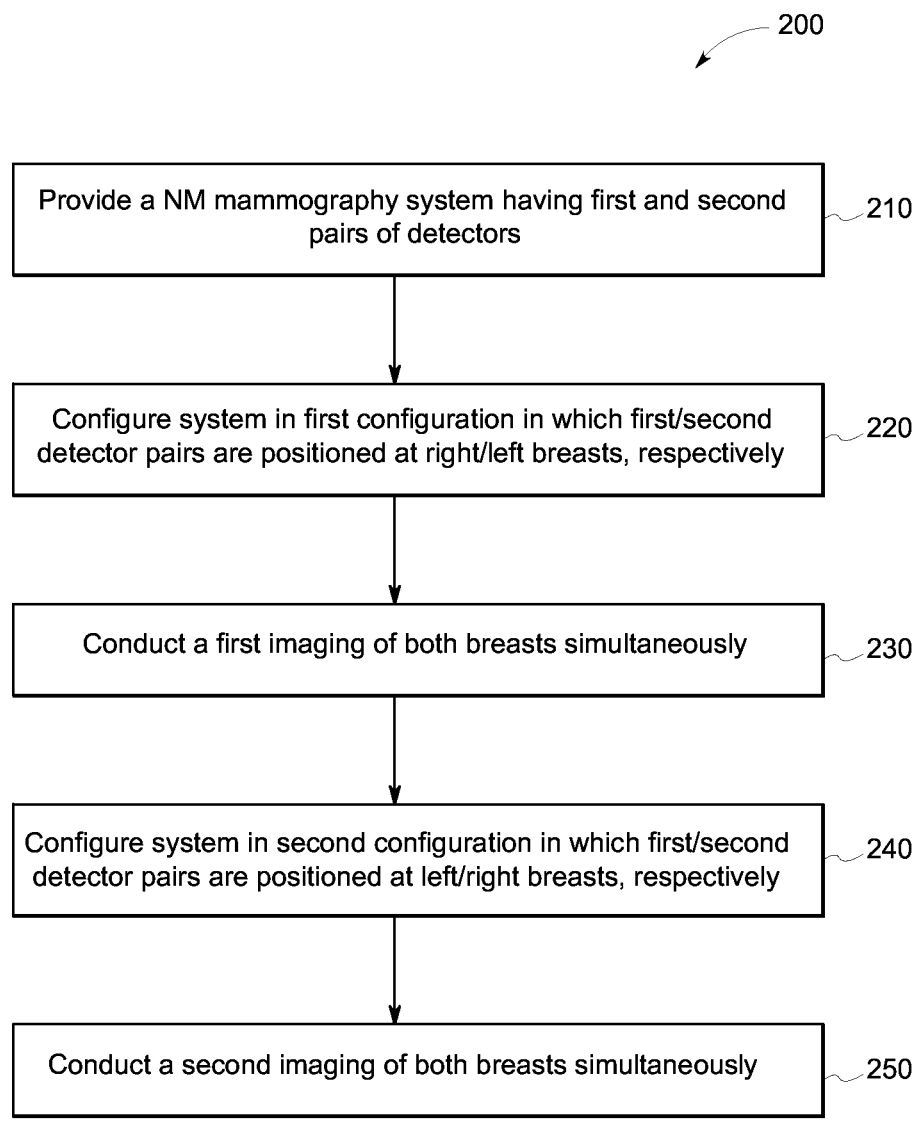
FIG. 16 is a flowchart showing the steps of yet another method according to one or more embodiments of the present invention.
Figure 17:
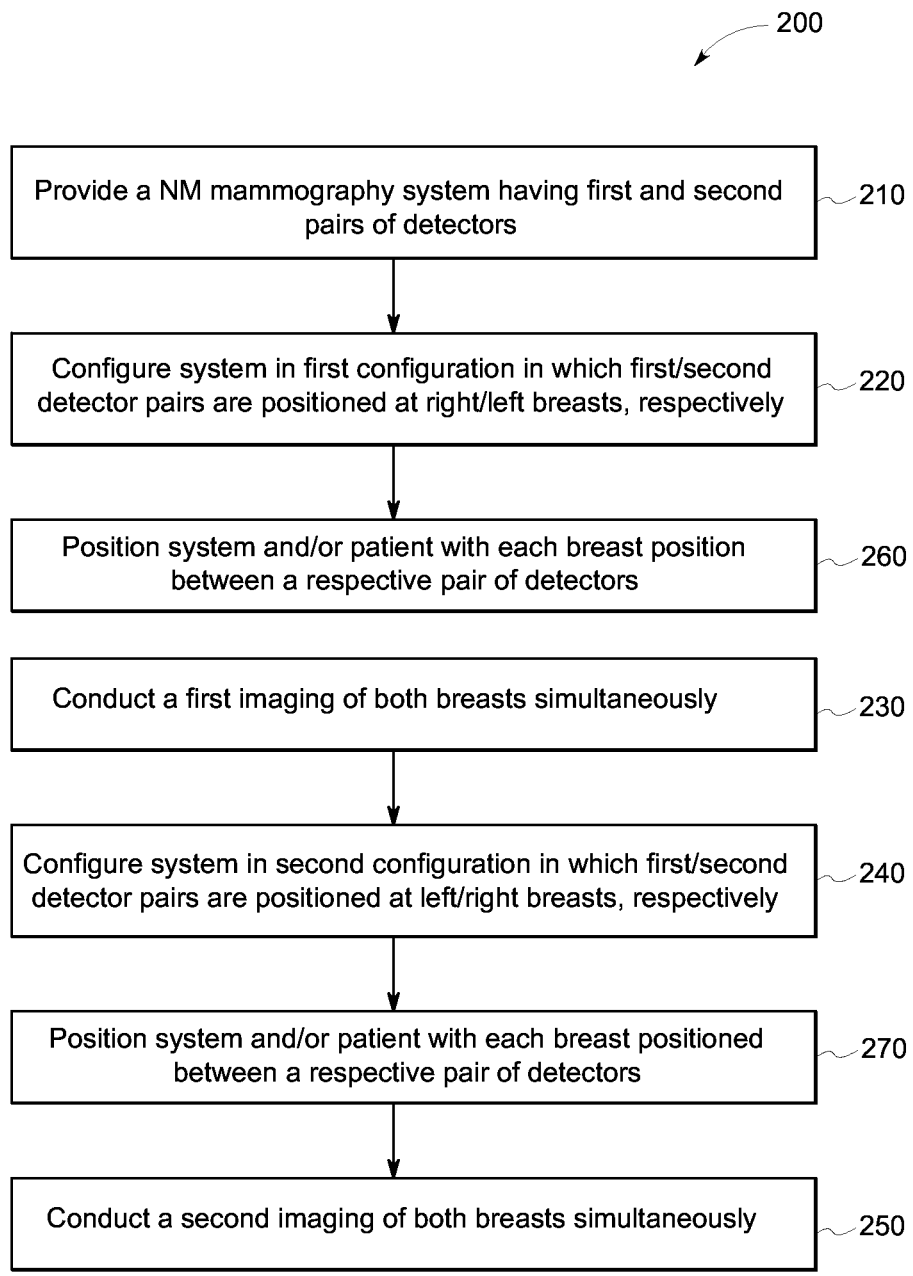
FIG. 17 is a flowchart showing the steps of still another method according to one or more embodiments of the present invention.

FIGS. 16 and 17 illustrate methods 200 for conducting examinations of both breasts of a patient utilizing one or more of the systems 30 described above, such as the third embodiment. The method 200 may comprise the steps of: (210) providing a nuclear medicine mammography system having first and second pairs of generally opposed articulatable gamma photon detectors operably connected to respective first and second platens, and a turntable operably connecting said first and second platens to a gantry; (220) configuring the system in a first configuration in which the first detector pair is arranged to image the right breast and the second detector pair is arranged to image the left breast; (230) conducting a first imaging of both breasts of the patient by concurrently operating both detector pairs; (240) configuring the system in a second configuration in which the first detector pair is arranged to image the left breast and the second detector pair is arranged to image the right breast; and (250) conducting a second imaging of both breasts of the patient by concurrently operating both detector pairs. As shown in FIG. 17, prior to each of steps (230) and (250), the method 200 may further comprise the step (260/270) of positioning the system (e.g., the detectors) and/or the patient such that each breast is positioned between a respective pair of detectors. One or both of the configuring steps may be performed by rotating or moving the turntable so as to place each platen and its associated detector pair in position for immobilizing and imaging a respective breast. The first detector pair is dedicatedly oriented in a first orientation and the second detector pair is dedicatedly oriented in a second orientation that is different from said first orientation. For example, one detector pair may be oriented in a cranio-caudal orientation and the other may be oriented in a mediolateral or mediolateral-oblique orientation. The configuring steps may include articulating one or both of the detectors in each detector pair so as to immobilize each respective breast for imaging.

The present invention may be used advantageously to facilitate biopsies and other procedures, such as excision, marker placement, etc. While the breast is immobilized between a respective pair of detectors, if a suspicious portion of tissue is discovered (e.g., by viewing the real-time or reconstructed MBI image), the tissue may be biopsied, tagged, removed or otherwise dealt with while the breast is immobilized.

The above description is intended to be illustrative, and not restrictive. While the invention has been described in terms of various specific embodiments, those skilled in the art will recognize that the invention can be practiced with modification within the spirit and scope of the claims. For example, the above-described embodiments (and/or aspects thereof) may be used in combination with each other. In addition, many modifications may be made to adapt a particular situation or material to the teachings of the invention without departing from its scope. (For example, while the present invention can be used to image both breast independently and concurrently, it is also possible to use the present invention to image the breasts non-concurrently, or to image only one breast without imaging the other.) While the dimensions and types of materials described herein are intended to illustrate the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable those skilled in the art to practice the invention, including making and using any devices or systems thereof and performing any methods thereof. It is the following claims, including all equivalents, which define the scope of the present invention.

The invention claimed is:

1. A nuclear medicine mammography system for conducting examinations of both breasts of a patient, comprising:
   first and second pairs of generally opposed articulatable gamma photon detectors, wherein each pair of detectors can be arranged to image a respective breast independently from the other pair of detectors,
   wherein the first detector pair is dedicatedly oriented in a first orientation and the second detector pair is dedicatedly oriented in a second orientation that is different from said first orientation,
   wherein the system is configured to provide a first configuration in which the first detector pair can be arranged to image the right breast and the second detector pair can be arranged to image the left breast, and a second configuration in which the first detector pair can be arranged to image the left breast and the second detector pair can be arranged to image the right breast,
   wherein in each of said first and second configurations both breasts can be imaged concurrently.

2. A nuclear medicine mammography system according to claim 1, wherein one detector pair is dedicated to a generally cranio-caudal orientation.

3. A nuclear medicine mammography system according to claim 1, wherein one detector pair is dedicated to a generally mediolateral-oblique orientation.

4. A nuclear medicine mammography system according to claim 1, wherein one detector pair is dedicated to a generally mediolateral orientation.

5. A nuclear medicine mammography system according to claim 1, wherein each detector pair is oriented in a respective orientation in both the first and second configurations.

6. A nuclear medicine mammography system according to claim 1, wherein one detector pair is oriented in a cranio-caudal orientation and the other is oriented in a mediolateral orientation.

7. A nuclear medicine mammography system according to claim 1, wherein one detector pair is oriented in a cranio-caudal orientation and the other is oriented in a mediolateral-oblique orientation.

8. A nuclear medicine mammography system according to claim 1, wherein one detector pair is oriented in a mediolateral orientation and the other is oriented in a mediolateral-oblique orientation.

9. A nuclear medicine mammography system according to claim 1, further comprising:
   first and second platens operably connected to said first and second detector pairs, respectively; and
   a turntable operably connecting said first and said platens to a gantry.

10. A nuclear medicine mammography system for conducting examinations of both breasts of a patient, comprising:
    first and second pairs of generally opposed articulatable gamma photon detectors;
    first and second platens operably connected to said first and second detector pairs, respectively;
    a turntable operably connecting said first and second platens to a gantry;
    wherein the first detector pair is dedicatedly oriented in a first orientation and the second detector pair is dedicatedly oriented in a second orientation that is different from said first orientation; and
    wherein the system is configured to provide a first configuration in which the first detector pair can be arranged to image the right breast and the second detector pair can be arranged to image the left breast, and a second configuration in which the first detector pair can be arranged to image the left breast and the second detector pair can be arranged to image the right breast.

11. A nuclear medicine mammography system according to claim 10, wherein in each of said first and second configurations both breasts can be imaged concurrently.

12. A nuclear medicine mammography system according to claim 10, wherein each pair of detectors can be arranged to image a respective breast independently from the other pair of detectors.

13. A nuclear medicine mammography system according to claim 10, wherein each detector pair is oriented in a respective orientation in both the first and second configurations.

14. A method for conducting examinations of both breasts of a patient, comprising the steps of:
    (a) providing a nuclear medicine mammography system having first and second pairs of generally opposed articulatable gamma photon detectors operably connected to respective first and second platens, and a turntable operably connecting said first and second platens to a gantry;
    (b) configuring the system in a first configuration in which the first detector pair is arranged to image the right breast and the second detector pair is arranged to image the left breast;
    (c) conducting a first imaging of both breasts of the patient by concurrently operating both detector pairs;
    (d) configuring the system in a second configuration in which the first detector pair is arranged to image the left breast and the second detector pair is arranged to image the right breast; and
    (e) conducting a second imaging of both breasts of the patient by concurrently operating both detector pairs.

15. A method according to claim 14, further comprising the step of:
    (f) prior to each of steps (c) and (e), positioning the system and/or the patient such that each breast is positioned between a respective pair of detectors.

16. A method according to claim 14, wherein one or both of said configuring steps is performed by rotating or moving the turntable so as to place each platen and its associated detector pair in position for immobilizing and imaging a respective breast.

17. A method according to claim 14, wherein the first detector pair is dedicatedly oriented in a first orientation and the second detector pair is dedicatedly oriented in a second orientation that is different from said first orientation.

18. A method according to claim 14, wherein one detector pair is oriented in a cranio-caudal orientation and the other is oriented in a mediolateral or mediolateral-oblique orientation.

19. A method according to claim 14, wherein said configuring steps include articulating one or both of the detectors in each detector pair so as to immobilize each respective breast for imaging.

* * * * *